US010337752B2

(12) United States Patent
Reichenbach

(10) Patent No.: US 10,337,752 B2
(45) Date of Patent: Jul. 2, 2019

(54) VENTILATION SYSTEM AND METHOD FOR AIR-CONDITIONING AN INTERIOR USING AT LEAST ONE SUCH VENTILATION SYSTEM

(71) Applicant: Albert Reichenbach, Iserlohn (DE)

(72) Inventor: Albert Reichenbach, Iserlohn (DE)

( * ) Notice: Subject to any disclaimer, the term of this patent is extended or adjusted under 35 U.S.C. 154(b) by 60 days.

(21) Appl. No.: 15/525,393

(22) PCT Filed: Nov. 17, 2015

(86) PCT No.: PCT/EP2015/076764
§ 371 (c)(1),
(2) Date: May 9, 2017

(87) PCT Pub. No.: WO2016/079088
PCT Pub. Date: May 26, 2016

(65) Prior Publication Data

US 2018/0180312 A1 Jun. 28, 2018

(30) Foreign Application Priority Data

Nov. 18, 2014 (DE) .................... 20 2014 105 531 U
Feb. 23, 2015 (EP) .................................... 15156137

(51) Int. Cl.
| | |
|---|---|
| *A61L 9/00* | (2006.01) |
| *F24F 7/007* | (2006.01) |
| *B01D 47/00* | (2006.01) |
| *F24F 7/08* | (2006.01) |
| *F24F 6/12* | (2006.01) |
| *F24F 7/06* | (2006.01) |
| *F24F 12/00* | (2006.01) |
| *A61L 2/22* | (2006.01) |
| *A61L 9/14* | (2006.01) |
| *F24F 13/06* | (2006.01) |
| *F24F 7/00* | (2006.01) |

(52) U.S. Cl.
CPC *F24F 7/08* (2013.01); *A61L 2/22* (2013.01); *A61L 9/14* (2013.01); *F24F 6/12* (2013.01); *F24F 7/065* (2013.01); *F24F 12/00* (2013.01); *F24F 12/006* (2013.01); *F24F 13/06* (2013.01); *F24F 2007/004* (2013.01); *F24F 2013/0608* (2013.01); *Y02B 30/563* (2013.01)

(58) Field of Classification Search
CPC ............... A61L 2/18; A61L 2/186; A61L 2/22
USPC ........ 422/1, 4–5, 28, 128, 305–306; 34/443, 34/523; 96/243
See application file for complete search history.

(56) References Cited

FOREIGN PATENT DOCUMENTS

| | | | | | |
|---|---|---|---|---|---|
| FR | 2847968 | A1 | | 6/2004 | |
| WO | 9906774 | A1 | | 2/1999 | |
| WO | WO 99/06774 | A1 | * | 2/1999 | ................ F24F 5/00 |

OTHER PUBLICATIONS

International Search Report dated Feb. 26, 2016 in parent application PCT/EP2015/076764.
Written Opinion of the International Searching Authority dated Feb. 17, 2017 in parent application PCT/EP2015/076764.
International Preliminary Report on Patentability dated Feb. 26, 2016 in parent application PCT/EP2015/076764.

* cited by examiner

*Primary Examiner* — Monzer R Chorbaji
(74) *Attorney, Agent, or Firm* — Polson Intellectual Property Law, PC; Margaret Polson

(57) ABSTRACT

A ventilation system comprising a conveying unit for conveying a supply airstream into an interior space through at least one air outlet channel, and at least one exhaust air opening which may have an adjustable opening width. The at least one air outlet channel arranged at a distance from the at least one exhaust air opening, such that an airstream is established during operation therebetween in the interior space. The ventilation system is paired with a humidifying device to supply humidity into the interior space, said humidifying device comprising a generator for generating an aerosol from a liquid with droplets sized to be carried by the airstream, and at least one aerosol outlet channel arranged in the interior space such that the aerosol is captured by the airstream. A method for conditioning an interior space using at least one or more such ventilation systems is further described.

18 Claims, 2 Drawing Sheets

VENTILATION SYSTEM AND METHOD FOR AIR-CONDITIONING AN INTERIOR USING AT LEAST ONE SUCH VENTILATION SYSTEM

BACKGROUND

The present disclosure relates to a ventilation system for an interior space, having a conveying unit for conveying a supply airstream into an interior space, said conveying unit feeding a supply airstream to at least one air outlet channel arranged in the interior space, and having at least one exhaust air opening, the opening width of which can be adjusted and through which exhaust air can exit the interior, wherein the at least one air outlet channel is arranged at a distance from the at least one exhaust air opening, such that an airstream is established during the operation of the ventilation system from the at least one air outlet channel to the at least one exhaust air opening in the interior. The present disclosure further relates to a method for conditioning an interior space.

Ventilation systems of this type are used for ventilating and/or conditioning interior spaces. The interior spaces being contemplated in this case can be any generally enclosed spaces, wherein this term also subsumes the interior space of an entire building or building section. As such, an interior space in the context of these embodiments can also be, by way of example, a section of a multi-process production process. These systems serve the purpose of supplying supply air into the interior space and discharging exhaust air. The supply air is typically fresh air or an airstream with a proportion of fresh air, the latter in cases where the exhaust airstream or a portion thereof is recirculated. Such a ventilation system comprises a supply air outlet, which according to a known design is constructed as one or more air outlet ducts. To obtain the most uniform possible air discharge over a certain interior space region, it is common for porous channels to be used as the air outlet, such as fabric tubes from which the supply airstream escapes, for example. The feed of supply air generates a slight overpressure in the interior space in the supply air outlet region.

At least one exhaust air opening is functionally assigned to the ventilation system. The cross-sectional area of the same through which air can flow is adjustable. Due to the overpressure which develops as a result of the supply air feed into the interior space, an airstream is established from the at least one supply air outlet toward the at least one exhaust air opening. For this reason, the supply air inlet and the exhaust air opening are spaced apart from each other. As a rule, such a ventilation system is arranged in the interior space in such a manner that the supply air outlet is positioned with respect to the height of the interior space at a lower level than the at least one exhaust air opening. As a result, supply air can be fed via the entire desired surface area of the interior space, and the exhaust air can be discharged through the at least one exhaust air opening by taking advantage of the chimney effect which sets in.

A ventilation system conceived in this manner not only supplies fresh air into the interior space, but also keeps the same clean because of the airstream which is established. Dust or other particulate matter is carried away by the exhaust airstream. For this reason, such ventilation systems are widely used in food-producing plants, such as bakeries—especially large bakeries. According to the suspended particles carried off by means of such an exhaust airstream, one or more filters can be included, wherein the exhaust airstream passes through the same before it—if it is not completely recirculated—is discharged via the exhaust air opening to the surroundings.

The ventilation system can have a heat recovery unit—a so-called recuperator—which removes heat from the exhaust airstream and releases it to the supply air. In this way, process heat generated in the interior space—such as during the operation of heat-emitting devices—can be used to feed heat to the supply air. In some cases, such a ventilation system additionally has a heater for independently heating the supply air fed by the same.

Ventilation systems of this type must sometimes be supplemented by a conditioning system if temperatures in the interior space can rise above an allowable temperature threshold either due to generated process heat or ambient heat.

In addition, it may be necessary to maintain the relative humidity in the interior space at a certain level, or adjust such a level. In such a case, a humidifier will be functionally assigned to the ventilation system. The humidity introduced in vapor form into the interior space can, however, result in the formation of condensation, which is undesirable, especially when such a ventilation system is used in a food manufacturing or processing plant.

Even in cases where such ventilation and/or conditioning systems achieve the desired purposes, they sometimes turn out to be complicated and costly to operate.

The foregoing examples of the related art and limitations therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Proceeding from this background, a problem addressed by the present disclosure is therefore that of advancing a ventilation system in the class as described above, as well as a method as described above, in such a manner that it is—most of all—cheaper to condition a space.

The problem with respect to the ventilation system is addressed according to the present disclosure by a ventilation system in the class as described above, wherein the ventilation system is paired with a humidifying device to supply humidity into the interior, said humidifying device comprising a mist generator for generating an aerosol from a liquid, with liquid droplets of a size allowing the same to be carried along with the airstream established in the interior, and comprising at least one aerosol outlet channel, which is arranged in the interior in such a manner that the emerging aerosol is captured by the airstream.

The problem with respect to the method is addressed according to the present disclosure by a method of the class as described above, wherein a supply airstream is introduced into the building through at least one air outlet channel, with a pressure which is higher than the pressure prevailing at this site with no supply airstream, said supply airstream being conveyed through the building or a part of the same to at least one exhaust air opening, and in that an aerosol is added to the supply airstream after the same exits from the air outlet channel, said aerosol having liquid droplets of a size allowing the same to be carried along by the airstream established in the building.

In the ventilation system according to the present disclosure—and the same applies to the disclosed method—humidity is introduced into the interior space in the form of an aerosol. For this reason, this ventilation system comprises a mist generator for generating the aerosol from a liquid. The generator can be, by way of example, an ultrasound nebulizer. Such an ultrasound nebulizer generates the liquid droplets in the desired size from a liquid film, by means of high-frequency mechanical vibrations. Piezoceramic elements which convert the electrical oscillations into the necessary mechanical vibrations can be used for this purpose, for example. The droplet size of the aerosol produced is sufficiently small so that they can be carried by an airstream as a suspended load. For this reason, the aerosol outlet arranged in the interior space with respect to the supply air outlet where the supply air emerges is arranged in such a manner that the emerging aerosol is captured by the airstream which is established during the operation of the ventilation system in the interior space. In addition, in this ventilation system, the droplet size of the aerosol is established in such a manner that the droplets can be carried by the airstream established in the interior space, and thus are held in suspension by the same. This interaction between the droplet size and the arrangement of the aerosol outlet with respect to the supply air outlet in the interior space prevents the formation of condensation. Most of all, surfaces which are vulnerable to condensation are stressed very little—if at all—by the fact that the supplied humidity is held in suspension in the manner described. This has a cost-reducing effect on the otherwise necessary measures for keeping such surfaces clean. It is further advantageous that the humidity can be supplied as an aerosol in a conditioned manner. This means that the supplied liquid droplets can be conditioned—that is, can contain, by way of example, biological or other additives, and also fragrances. Such biological additives can be, for example, anti-microbial and/or antifungal agents. These are preferably micellized natural substances. The supply of ambient humidity in the form of an aerosol is especially advantageous in the food industry, since packaging in such an environment can have a prolonging effect on the average shelf life. In addition, a food which has been packaged in such an environment appears more attractive to customers.

Since the humidity supplied as an aerosol is not deposited as a condensate in the interior space, suspended substances are bound by the liquid droplets and carried away by the airstream of the interior space or interior region which must be kept clean and/or conditioned.

The concept described above not only allows quickly and specifically reacting to changes in humidity in the interior space. It is also possible with this concept to keep the humidity very constant, and/or to adapt the humidity to changing environmental conditions, via a corresponding control of the aerosol feed, in the desired range of 50 to 55 percent. The humidity in the interior space can, if desired, also be set to a higher value.

For humidification of an interior space, sterile water is typically used for aerosol generation. So that the droplets can be carried along by the airstream which is established during the operation of the ventilation system in the interior space, they typically lie within the size range of 1 to 5 μm, but can reach sizes of about 20 μm if desired.

In order to achieve uniform ventilation over the interior region being ventilated, in one embodiment of a ventilation system, the at least one air outlet channel is designed as a fabric tube. Typically, several such textile tubes are arranged at a certain height of the interior space. These can have different cross-sectional geometries, as well as different geometries in their longitudinal extension. The geometries of the longitudinal extension should be adapted to the conditions of the space. The supply air passes through the fabric walls through such a textile tube. This achieves a planar emergence of the supply air. The supply air emerges with a certain overpressure, and as a result a certain overpressure is created in the interior space being ventilated, into which the supply air is discharged. This overpressure prevails upon continuous operation of the ventilation system. The supply air is supplied to the air outlet channel(s) via feed pipes. The conveying unit used to convey the supply air is typically positioned outside of the interior space, most commonly on the building roof.

In one embodiment of the supply air outlet, the aerosol outlet is likewise designed as a channel, such as a tube, using one or more fabric tubes, and specifically in such a manner that such an aerosol outlet tube extends parallel to an air outlet channel and runs at a short distance from the same. Advantageously, the aerosol outlet is arranged just above the supply air outlet, so that emerging aerosol essentially falls into the airstream established in the interior space, starting at the supply air outlet, due to gravity, and is then captured and carried along by the airstream. In this respect, it is advantageous that the supply airstream does not emerge from individual nozzles or ports, but rather through the entire, or a significant portion of, the outer surface of such a fabric tube. This emerging supply airstream, which already has a sizeable volume due to the aforementioned outlet, incorporates the aerosol spray emerging from the aerosol outlet and carries it along as a suspended load.

It is advantageous for the operation of such a ventilation system if a certain chimney effect is established in the interior space being ventilated. This effect is established, by way of example, if process heat is produced in the interior space. This is achieved by the supply air outlet being arranged at a lower level with respect to the height of the interior space than the at least one exhaust air opening. A combination of these measures is also possible.

It should be understood that such a ventilation system may extend over several floors in the interior space, which can be connected to each other.

The components necessary for the operation of the ventilation system may all be functionally assigned to the feed unit. This includes the air conveyor pump needed for conveying the supply air and the mist generator. The mist generator is connected to a liquid supply. As a general rule, additional air filters are used to supply filtered supply air to the interior space. If a recovery of heat from the exhaust airstream is intended, the at least one heat recovery unit needed for this purpose may be likewise functionally assigned to the conveying unit, such that all elements are arranged together in one assembly.

In one embodiment, a conveying unit housed as an assembly of the necessary elements is on supports, typically on the roof of a building. The components of such a conveying unit are arranged in the housing so that they can be taken out, cleaned and/or replaced—in particular the filters. An arrangement of the conveying unit with its housing on supports is may be advantageous if an internal cleaning of the individual units and/or the housing using a liquid is anticipated. In this case, the housing is positioned in a trough, or a liquid capturing channel is positioned on the bottom of the housing running around the periphery thereof.

Both serve to capture cleaning liquid. One or more drain openings are included so that the liquid does not unintentionally overflow out of the liquid capturing channel or the trough. The cleaning water can leave these and then, if the conveying unit is located on the roof of a building, be fed to the roof drainage. It is possible in such a configuration for a line to be connected to the at least one drain opening, such as a tube or a hose, through which the cleaning wastewater is disposed of—and for example fed to a cleaning water processing system.

According to a further embodiment, the ventilation system is integrated into a production facility situated in a building.

An aerosol, which is equipped with biological additives, by way of example, can be made to supply fungicides to one or more work areas, for example, if this is necessary or useful. Such a measure is expedient in, for example, a work area which is a cleaning or washing station in which containers are cleaned or washed, for example, the same then serving as transport containers for food. In this way, it is possible to effectively counteract the formation of mold, for example on the walls, taking advantage of the special distribution of the supplied aerosol inside a work area. Such a work area treatment is may be performed when the operation is halted in that work area.

Fragrances can be also be supplied for the purpose of conditioning. This makes sense, for example, in retail spaces to facilitate shopping behavior.

The supply of humidity in the form of an aerosol has an advantageous effect for, by way of example, rising dough in a bakery as the production facility, with the aerosol lying on the same in a thin film. This improves not only the quality of the dough and the baking product, but, as already indicated above, also the average shelf life within which the dough should be baked.

The work areas in such a manufacturing facility may be set up to match the design of the ventilation system and the interior space humidifying unit assigned to the same. For instance, the working areas in which there should be the most constant possible air pressure and particular cleanliness may be located directly beside the air outlet channels. Due to the airstream established in the building, the work areas which are arranged facing the exhaust air opening(s) in the airstream direction may be used for operations in which there are not such high demands for the air pressure and cleanliness, so that these need not be positioned directly beside one or more air outlet channels.

In the event that there is a supply air feed via the air outlet channels present in different work areas which should be independent in these areas from other work areas, and there is also an aerosol feed, a separate conveying unit comprising a pump for the supply air feed as well as a mist generator for generating the aerosol may be functionally assigned to each such work area. Even if several conveying units are required in this way for the overall ventilation and conditioning of the building, such an arrangement of the production facility enables independent control of the local conditions in different work areas. In addition, commercial units can be utilized in such a case, such that the total cost of such a system does not exceed expectations.

A clever layout of the building of the production facilities to enable one or more airstreams, and the utilization of the process heat of individual production machines as an airstream motor, allows operation of the ventilation and conditioning system of such production facilities with very low costs compared to the costs for setting up and operating conventional ventilation and conditioning systems.

So that the airstream can form within the building of the production facility, the same is built sufficiently tight, such as in the manner of a low-energy building. A lock is typically provided between the areas of different pressure for doors and gates between two different pressure areas in the building, and/or to the outside.

Such a production facility may have multiple work areas in the building, which are typically separated from one another by walls. However, this is not absolutely necessary and is subject to the duties to be performed in a work area. One or more air outlet channels are arranged, typically together with corresponding aerosol outlet channels, in work areas where there are elevated requirements for a constant air pressure and cleanliness. In the individual work area, the supply air feed and the aerosol feed can be adjusted independently of other work areas, by means of an air- and aerosol supply. In this way, adjustments can be made with respect to the desired air pressure in the work area and the desired humidity in a work area, independently of the requirements in other work areas. Due to the ventilation concept in such a facility, there is an airstream routing from each work area up to the exhaust air openings of the building. These may be located at the end of an exhaust airstream duct via which exhaust air is conveyed to the exhaust air valves. In this way, such an exhaust airstream duct constitutes a collector for the airstream generated by the overpressure in the work area and/or individual work areas. In order to achieve this, work areas which are enclosed by walls are connected by a flow of air to such an exhaust airstream duct. This can be realized, by way of example, by the work areas in a production level having airflow openings in their walls. It should be understood that these must be large enough that the desired airstream can form due to the typically very small pressure difference between the pressure near the air outlet channels and the exhaust air opening(s). An airstream which leaves each work area at the top thereof is also possible. For a production facility with several production levels, this can be achieved, by way of example, by ceiling openings in the manner of headspace vents. It should be understood that a combination of these measures can also be used to realize the desired airstream routing.

The individual work areas, which can certainly differ from each other in ceiling height even if located on one level, are preferably separated by flow barriers. This serves the purpose of controlling the airstream transition from one work area into another work area. This can be implemented, by way of example, by bulkheads suspended from the ceiling.

Such a ventilation and conditioning system functions particularly effectively, and most of all, efficiently, if several production levels are included in the production facility, and one or more production machines which release process heat are needed for the production process. In the case of a bakery, the production machines which release process heat are, for example, the ovens used—particularly if feed ovens are used as the baking ovens. For airstream generation and/or to support the airstream which is established solely on the basis of the ventilation system, these production machines may be set up in such a production facility in a location where the airstream, or at least a portion thereof, flows past. The air convection due to the process heat supports the airstream established in the building. For this reason, such a production machine which releases process heat may be arranged in a building with several production levels in an upper production level, close to or even next to an exhaust airstream duct. The chimney effect which arises in such a production facility equipped with such a ventilation system is significantly enhanced by such a measure. Because such a production machine which releases process heat as the motor of the airstream is available, the supply airstream, and specifically its pressure, can be adjusted to a wider range without the need to fear that an airstream between the air outlet channel(s) and/or the exhaust air opening(s) will stop. As such, an airstream may be created which also has lower pressures and/or pressure differences between the supply air and the exhaust air opening, whereas an airstream which fulfills desired purposes would not be established between the air outlet channel(s) and the exhaust air opening(s) without a production machine which releases process heat as the airstream motor.

One or more such fabric tubes may be arranged as air outlet tubes in the work area, or in individual work areas, at a certain height. These can be of different cross-sectional geometries, and can have different geometries in their longitudinal extension. The geometries of the longitudinal extension should be adapted to the conditions of the space. The supply air passes through the fabric walls through such a textile tube. This is the result of a certain overpressure, with the effect that a certain overpressure prevails in the space being ventilated, into which the supply air is discharged. The supply air is supplied to the air outlet channel(s) via feed pipes. Typically, the conveying unit required for this purpose is positioned outside the building, most commonly on the building roof.

In one embodiment of the supply air outlet, the aerosol outlet is likewise designed as a channel, such as a tube, using one or more fabric tubes, and specifically in such a manner that such an aerosol outlet tube extends parallel to an air outlet channel and runs at a short distance from the same. The aerosol outlet may be arranged just above the supply air outlet, so that emerging aerosol essentially falls into the established airstream, starting at the supply air outlet, due to gravity, and is then captured and carried along by the airstream.

Such a production facility may be constructed with the most homogeneous surface possible, with a low thermal transmittance coefficient, therefore specifically using the so-called low-energy building standards, and process heat may be exploited for heating the supply air, if necessary, and/or for other production processes providing heat. The design of a production facility with such a standard is therefore achieved by coming in below the technical specification values overall for energy efficiency. According to one embodiment, the established airstream(s) is/are monitored for their respective temperatures. In addition, the air pressure may be monitored for the work areas in which there should be the most constant possible air pressure. For the purpose of heat balancing, the airstream quantity and its temperature may likewise be monitored. The data of the sensors used for this purpose is fed to a central control unit, which then in turn accordingly control the corresponding actuators to react to variations in the desired temperature, the desired air moisture content, and the desired air pressure.

As part of the operation of such a ventilation system, especially in areas with a larger number of people, such as in school, offices or cafeteria spaces, cooling can be performed by the supply of fresh air to accordingly reduce the $CO_2$ concentration, which counteracts premature fatigue.

The lines, and in particular the aerosol lines, are typically sterilized regularly, for example with ozone.

In order to counteract the accumulation of condensation in the aerosol line, should this actually occur, these lines can be laid with a certain gradient.

Such a production facility can be operated particularly efficiently if it is designed to have a certain storage capacity for the climate variables temperature, humidity and pressure. With respect to the humidity, this can be achieved by providing a certain amount of storage mass, for instance via the walls. Regarding the pressure tightness, this can be realized by bulkheads, locks, or the like in addition to an outer seal as already described. The walls, and objects located in a work area, can likewise be used as temperature buffers. In the context of a control of the work areas of the production facility with respect to these climate variables, the ventilation feed and venting are controlled.

With such a ventilation system, should this be necessary, it is possible to compensate for air pressure fluctuations in the environment. The airstream established in the interior space, generated by the supply air supplied with a certain overpressure, is exploited. As such, it is possible to counteract to a certain extent, in the entire interior space or in parts thereof, the pressure differences in the external environment, which are typically weather-related, via the pressure at which the supply air is supplied.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE DRAWINGS

The present disclosure is further described below in reference to the accompanying figures.

Before further explaining the depicted embodiments, it is to be understood that the invention is not limited in its application to the details of the particular arrangements shown, since the invention is capable of other embodiments. It is intended that the embodiments and figures disclosed herein are to be considered illustrative rather than limiting. Also, the terminology used herein is for the purposes of description and not limitation.

DETAILED DESCRIPTION

The ventilation and conditioning principle as used in the claimed production facility will be explained first with reference to FIG. 1.

Figure 1:
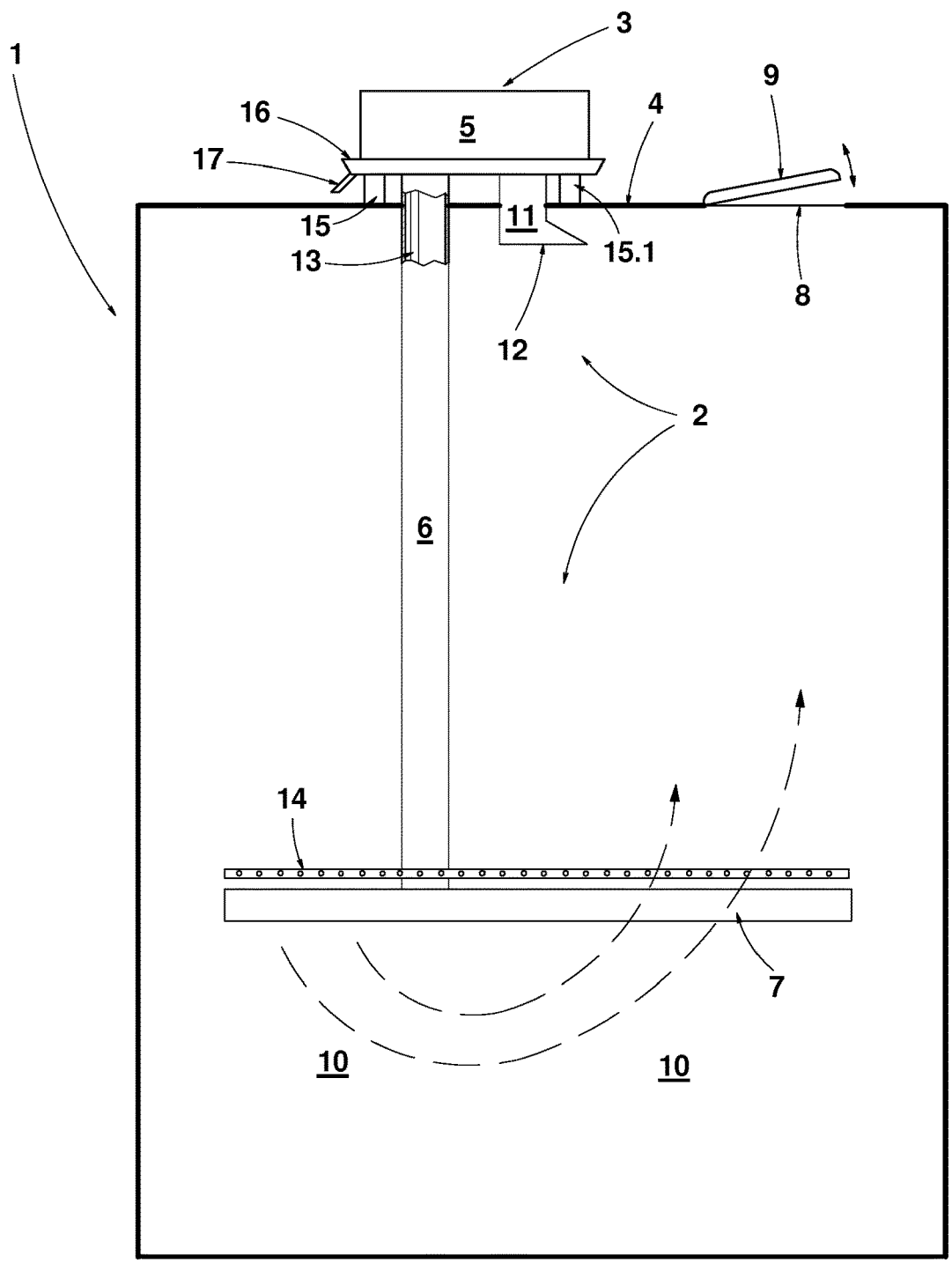
FIG. 1: shows a vertical section through a building having a ventilation system.

FIG. 1 shows a highly schematic illustration of a vertical section through a building 1 having a ventilation system 2. The ventilation system 2 has a conveying unit 3 which is placed on the roof 4 of the building 1. The individual parts of the conveying unit 3 are arranged in a shared housing 5, and are not illustrated in greater detail in FIG. 1. The conveying unit 3 has an air conveying pump by which the supply air is conveyed into a supply air line 6. The conveying unit 3 also comprises at least one filter through which the supply air removed from the surroundings is filtered before the same is fed into supply air line 6. The conveying unit 3 and/or the air conveyor pump contained therein is connected by the supply air line 6 to an air outlet channel 7. The air outlet channel 7 of the embodiment shown is a fabric tube, which is known in and of itself. The supply air conveyed in the supply air line 6 is pushed out of the fabric tube due to the porous nature of the walls thereof.

At least one exhaust air opening 8 is functionally assigned to the ventilation system 1. In the illustrated embodiment, this is realized by an exhaust air valve 9, the opening width of which can be adjusted, as can, consequently, the cross-sectional area thereof through which air can flow. It should be understood that the exhaust air valve 9 is only shown by way of example as an element used for adjusting the opening width of the exhaust air opening 8. Lamellas or other actuators which change the opening width of the exhaust air opening can be used in this position as well. Also, the exhaust air opening 8 need not be located in the roof 4 of the building as shown in the illustrated embodiment. It can also be arranged on one or more side walls thereof. According to the position of the exhaust air valve 9, the exhaust air opening 8 is larger or smaller, so that the airstream discharged to the surroundings can be established by the position of the exhaust air flap 9. The adjustability of the exhaust air flap 9, which in the illustrated embodiment is achieved by an electric servomotor, is indicated by the double arrow drawn adjacent thereto in FIG. 1.

The conveying unit 3 also has a recirculation path, via which the exhaust air can be guided by the conveying unit 3. Such a path can be designed to feed exhaust air to the supply airstream and/or to remove heat from the exhaust air vortex of a heat exchanger unit and transfer the heat to the supply air. The latter is especially useful if process heat is generated in the interior space 10 of the building and has to be dissipated. It can then be used to heat, by way of example, cold supply air from the surroundings during winter months. Such a heat recovery has a positive effect on the energy balance for an operation of the ventilation system, and thus on the operating costs of the building 1. An exhaust air vent 11 is functionally assigned to the conveying unit 3 to initiate such a recirculating exhaust airstream, and is arranged with its opening 12 slightly below the ceiling 4 of the building 1. According to the position of the exhaust air valve 9, the exhaust airstream and/or exhaust airstream fraction entering the exhaust air vent 11 can be adjusted.

The conveying unit 3 further comprises a mist generator for generating an aerosol. The aerosol is fed via an aerosol supply line 13 to an aerosol outlet tube 14 arranged in the interior space 10. In the illustrated embodiment, the aerosol supply line 13 is arranged inside of the supply air line 16, and is routed out of the supply air line 6 at the height of the aerosol outlet tube 14 in a manner which is not shown. The aerosol outlet pipe 14 has openings from which supplied aerosol emerges. The aerosol outlet tube 14 is located in relation to the height of the interior space 10 at a small distance above the air outlet channel 7, which is designed as a fabric tube. The emerging aerosol then falls due to gravity past the air outlet tube 7 into the airstream established between the air outlet tube 7 and the exhaust air opening 8 and/or the exhaust air vent 11. The droplet size generated by the mist generator is sufficiently small so that the aerosol droplets are carried along by this airstream as a suspended load. The established airstream is indicated schematically in FIG. 1 in the region of the left part of the air outlet tube 7. This schematic representation of the airstream is intended to show that it is guided through the interior space 10 of the building 1 being ventilated and then rises upward toward the exhaust air opening 8. As such, the air outlet tube 7 is at a considerably lower level than the exhaust air opening 8 in relation to the height of the building 1.

A supply of the humidity in the form of minute liquid droplets of an aerosol leads not only to a supply of humidity into the interior space 10. Rather, the supply of humidity in this form also leads to an adiabatic cooling at the same time. Process heat created in the interior space 8 is thus not only removed by the exhaust airstream, but is also cooled. The cost is accordingly low in the event that the interior space 10 must also be conditioned—that is, cooled.

The conveying unit 3 situated in the housing 5 is placed on the roof 4 of the building 1 on supports 15, 15.1. The housing 5 is arranged in a liquid collecting trough 16. The trough 16 has a drain port to which a drain pipe section 17 is connected. The provision of the trough 16 and the drain pipe section 17 serves the purpose of conveying cleaning liquid, applied for the interior cleaning of the housing 5 and/or the assemblies contained therein, in a targeted manner to the existing roof drainage.

FIG. 2 shows a production facility 18 with a multi-story building 19, wherein two production floors 20, 21 are included in the illustrated embodiment. The production facility 18 is a bakery with an integrated pastry shop. In addition to building 19, the production facility 18 has a ventilation system 22 which is constructed as the ventilation system 2 of the building 1. The ventilation system 22 comprises a plurality of conveying units 23, 23.1, 23.2, 23.3 which feed supply air and aerosol via supply air lines to each air outlet tube, each with at least one aerosol outlet tube functionally assigned to the same. These units of the ventilation system 22 are only shown in the production facility 18, for clarity's sake, with their components which are necessary to understanding the description of the present disclosure, in contrast to the ventilation system 2. The conveying units 23, 23.1, 23.2, 23.3 are arranged on the roof of the building 19. In the production facility 18, the ventilation system 22 comprises a plurality of conveying units 23 to 23.3, such that a different work area climate can be established in different work areas and can be controlled independently of the other work areas. As such, the air outlet tubes along with the aerosol outlet tubes of the individual conveying units 23 to 23.3 are situated in different work areas and also on different production floors 20, 21. In the building 19, the respective air outlet tubes are indicated, together with the respective aerosol outlet tubes, with the numerals 24 to 24.4. While the air- and aerosol outlet tubes 24 fed by the conveying unit 23 are situated in the upper of the two production floors 20, 21, the remaining air- and aerosol outlet tubes 24.1 are arranged in the lower production floor 20. The air- and aerosol outlet pipes 24 to 24.4 are each situated in different work areas of the building 19 at a height where the production and passage traffic is not disturbed thereby.

The conveying unit 23 feeds air to both the air- and aerosol outlet tube 24 of the upper production floor 20 and the air- and aerosol outlet tube 24.1 of a work area in the lower production floor 20. This occurs in a context where, in the illustrated embodiment, these two work areas should have the same climatization and the same work area pressure. For example, the work area paired with the air- and aerosol outlet tubes 24 is a baking preparation area. In this work area, dough pieces are created and stored for rising before they are placed into a baking oven 25 designed as a continuous oven. The baking oven 25 is also located on the upper production floor 21, adjacent to the work area just described. The ceiling 26 separating the two production floors 20, 21 is perforated in a section thereof to form an air space. This passage 27 serves the purpose of providing an airstream path from the lower production floor 20 into the upper production floor 21. An elevator shaft 28 with an elevator 29 positioned in the representation of FIG. 2 on the lower production floor 20 is used in this embodiment as a collection duct to collect the generated airstreams and release the same as exhaust air from the roof 30 of the elevator shaft 28. Several exhaust air valves 31, 31.1 can likewise be adjusted, with regard to their opening width, just like the exhaust air valve 9 of the ventilation system. The airstreams generated in the building 19 are influenced according to the adjustment of the opening width of the exhaust air valves 31, 31.1.

Figure 2:
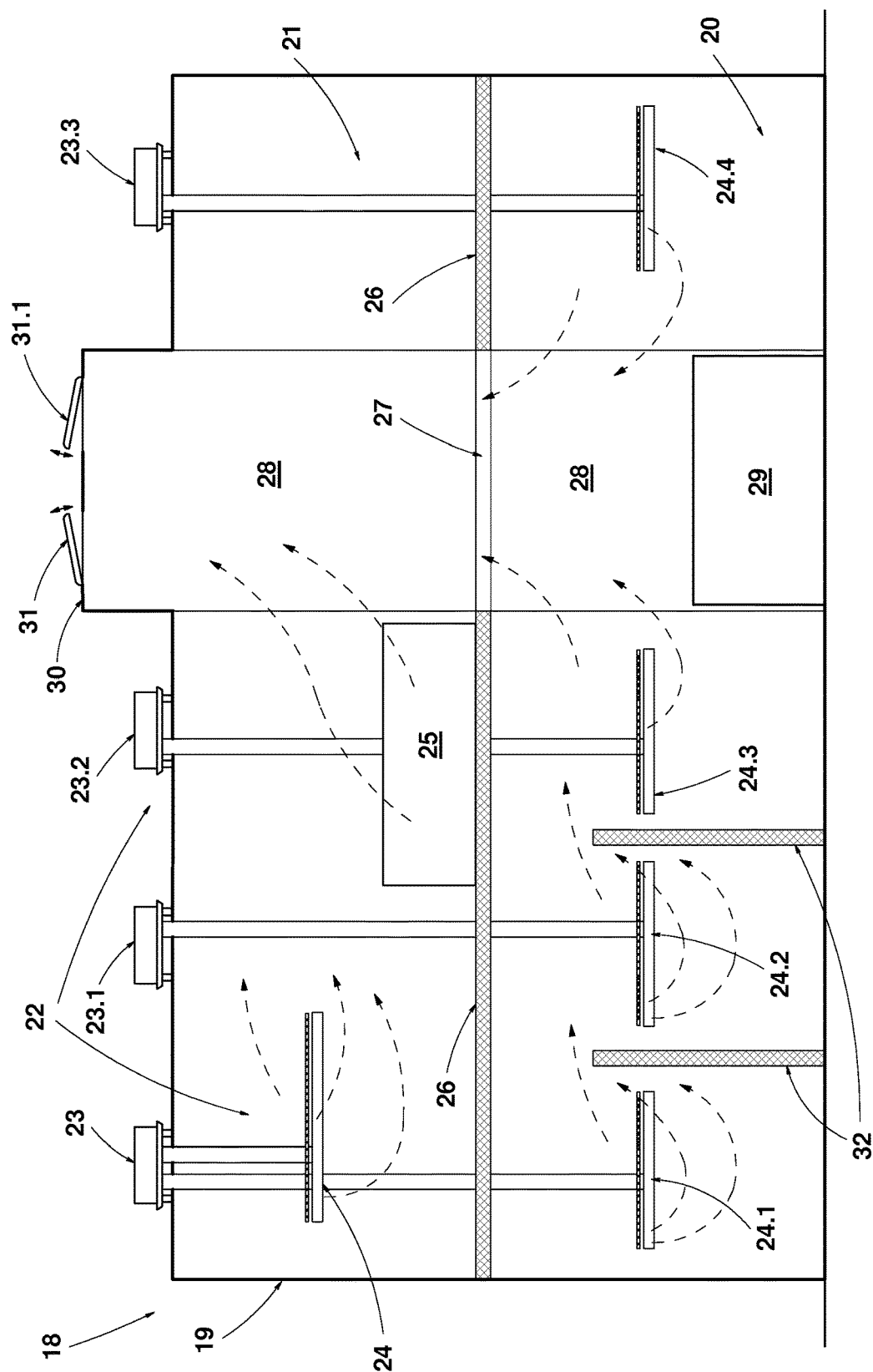
FIG. 2: shows a vertical section through a building of a production facility having a ventilation and conditioning system operating according to the principles of the ventilation system of FIG. 1.

Not shown in FIG. 2 is a heat recovery from the exhaust airstream, the heat being used to heat the supply air and/or feed the same to production steps which require heat, if necessary. A return feed can be established in this regard, the principle of which is described in the context of the ventilation system 2 of FIG. 1.

The air- and aerosol outlet tubes 24.1, 24.2, 24.3, 24.4 present on the lower production floor 20 each produce an airstream according to the principles described above. In FIG. 2, the airstreams established during operation of the ventilation system 2 are represented by dashed arrows. The work areas which are each paired with the air- and aerosol outlet tubes 24.1 to 24.4 are separated from each other by walls 32. In the illustrated embodiment, the walls 32 do not extend to the ceiling 26. The remaining headspace is used as a flow passage such that each airstream flows from each of the air- and aerosol outlet tubes 24.1, 24.2, 24.3, 24.4 to the elevator shaft 28 used during operation of the ventilation system 2 as an exhaust air collector duct. In the illustrated embodiment, the work areas of the air- and aerosol outlet tubes 24.1, 24.2 serve as work preparation areas. The work area with the air- and aerosol outlet tube 24.3 is designed as a pastry shop. On the other side of the elevator shaft 28, there is a work area in which the air- and aerosol outlet tubes 24.4 are arranged. This work area is set up as a rinsing and cleaning area. In this space, transport containers, typically plastic containers, may be rinsed after use to then be available again for use in the production process.

Operation of the oven 25 releases a significant amount of process heat. The heat necessarily rises, specifically into the elevator shaft 28. Due to the corresponding convection, a manner of wake is created in the cooler regions, particularly on the lower production floor 20 and in the work area into which the air- and aerosol outlet tube 24 opens. Consequently, the oven 25 functions during operation as an airstream motor. The production facility 18 may operate in principle 24 hours a day. Therefore, the oven 25 used as the airstream motor may be continuously or quasi-continuously in operation.

The airstreams established in the building 19 initially extend, starting from each air outlet tube, as seen in FIG. 2, mainly in the horizontal direction toward the elevator shaft 28 serving as a collecting duct, and then vertically upwards to the exhaust air valves 31, 31.1.

The air- and aerosol outlet tubes fed by each conveying unit 23 to 23.3 can be controlled independently by the same. This allows the establishment of a different overpressure near the air outlet tubes in each work area into which air is fed by a conveying unit 23 to 23.3, the establishment of an independent work area humidity, and the establishment of a different ambient pressure setting in each work area.

It should be understood that for the described operation of the ventilation systems 22, the building 19 is sufficiently airtight to the outside, such as in the manner of a low energy building.

The supply of work area humidity in the form of aerosol makes it possible to use the same as a carrier to supply biological substances in a work area. For example, in the illustrated embodiment, the conveying unit 23.3 may dispense biologically activated aerosol from the aerosol outlet tube of the air- and aerosol outlet tubes 24.4. These air- and aerosol outlet tubes 24.4 are located in the "rinsing" work area. Due to the high humidity, there is a general risk of sooting. The aerosol supplied to this work area is charged with a fungicide at intervals, typically when the rinsing process is on standby. For this reason, the rinsing work area is separated by the elevator shaft 28 serving as an exhaust airstream collector duct from the work areas for food processing.

The invention has been described with reference to embodiments. Without departing from the scope of the applicable claims, numerous other embodiments useful to realizing the invention will be apparent to a person skilled in the art. While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations, which are within their true spirit and scope. Each embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and sub-combinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

LIST OF REFERENCE NUMBERS 1 building
2 ventilation system
3 conveying unit
4 roof
5 housing
6 supply air line
7 air outlet tube
8 exhaust air opening
9 exhaust air valve
10 interior space
11 air vent
12 opening
13 aerosol supply line
14 aerosol outlet tube
15, 15.1 support 16 trough
17 drain pipe section
18 production facility
19 building
20 production floor
21 production floor
22 ventilation system
23, 23.1, 23.2, 23.3 conveying unit
24, 24.1, 24.2, 24.3, 24.4 air- and aerosol outlet tubes
25 oven
26 ceiling of the level
27 opening
28 elevator shaft
29 elevator
30 roof
31, 31.1 exhaust air valve
32 wall

The invention claimed is:

1. An arrangement comprising:
an interior space and a ventilation system, said ventilation system having a conveying unit for feeding a supply airstream from outside of the interior space through the ventilation system to at least one air outlet channel arranged in the interior space, wherein the ventilation system has a recirculation path via which the airstream in the interior space can be fed entirely or partially to the conveying unit, and said interior space having at least one exhaust air opening with an adjustable width through which exhaust air can exit the interior space,
wherein the at least one air outlet channel is arranged at a distance from the at least one exhaust air opening, such that an airstream is established during the operation of the ventilation system from the at least one air outlet channel to the at least one exhaust air opening in the interior space,
wherein the ventilation system further comprises a humidifying device for supplying humidity into the interior space, said humidifying device comprising:
an ultrasound nebulizer comprised by the conveying unit for generating an aerosol from a liquid, said aerosol having liquid droplets which are sized to be carried by the airstream established in the interior space,
an aerosol feed for supplying the aerosol to at least one aerosol outlet channel, and
at least one aerosol outlet tube arranged in the interior space, each aerosol outlet tube arranged with respect to its longitudinal extension parallel and in functional proximity to an air outlet channel, such that the aerosol emerging from each aerosol outlet tube is captured by the airstream emerging from the air outlet channel in proximity.

2. The arrangement of claim 1, wherein the at least one air outlet channel is a fabric tube.

3. The arrangement of claim 1, further comprising a heat recovery unit associated with the conveying unit to remove heat from the recirculating airstream fed to the conveying unit, thereby taking heat from the recirculating airstream and transferring heat to the supply airstream without feeding the recirculating airstream relayed back to the conveying unit into the supply airstream.

4. The arrangement of claim 1, wherein the at least one air outlet channel is arranged in relation to the height of the interior space at a lower level than the at least one exhaust air opening.

5. The arrangement of claim 1, wherein the conveying unit of the ventilation system is separated by a ceiling from the interior space.

6. The arrangement of claim 1, wherein a biological active agent is added to the aerosol.

7. The arrangement of claim 1, wherein the interior space is a production facility comprising an enclosed building with a plurality of work areas.

8. The arrangement of claim 7, wherein the enclosed building has multiple floors due to the provision of at least two production levels, the floors are connected to each other by at least one flow passage to allow passage of the airstream generated by the ventilation system, there are one or more work areas on the lower production level and one or more additional work areas on the production level situated above the lower production level, and the at least one air outlet channel is arranged in the lower production level.

9. The arrangement of claim 8, wherein the lower production level in which the at least one air outlet channel is arranged is divided into work areas delimited by walls, said work areas connected to each other by at least one flow passage to allow the passage of the airstream generated by the ventilation system.

10. The arrangement of claim 8, wherein at least one work area has a production machine which releases process heat arranged therein, said at least one work area situated on a production level above the lower production level.

11. The arrangement of claim 10, wherein the production machine is positioned within the production level such that the airstream generated by the ventilation system at least partly flows past the production machine.

12. The arrangement of claim 7, wherein the enclosed building has at least one production level divided into at least two work areas delimited by walls, at least one air outlet channel with an aerosol outlet channel functionally assigned thereto arranged in each of the at least two work areas, and wherein a supply airstream can be fed to said at least one air outlet channel in each work area, said at least one air outlet channel in each work area arranged independently of air outlet channels arranged in other work area(s).

13. The arrangement according to claim 12, wherein the at least one production level comprises at least two production levels separated by one or more floors, the at least two production levels connected to each other by at least one flow passage between the floors to allow the passage of the airstream generated by the ventilation system.

14. A method for conditioning an interior space using the ventilation system of claim 1, comprising:
introducing a supply airstream into a building through at least one air outlet channel with a pressure higher than a pressure prevailing at this location with no supply airstream, said supply airstream conveyed through the building or a part thereof to at least one exhaust air opening, and
adding an aerosol to the supply airstream after the same emerges from the at least one air outlet channel, said aerosol having liquid droplets sized to be carried by the airstream established in the building.

15. The method of claim 14, wherein the interior space being conditioned has at least two levels and the airstream established by the operation of the ventilation system flows through the building at least partially vertically.

16. The method of claim 15, wherein the airstream is supported in at least one vertically flowing section by one or more production machines which release process heat.

17. The method of claim 14, wherein the supply air and the aerosol are supplied to a production level of the building in a plurality of work areas which are separated from each other by walls, wherein a feed of supply air and/or aerosol is established in each work area independently of the feed of supply air and/or aerosol in the other work areas.

18. The method of claim 14, wherein the aerosol is mixed with a biological active agent.

\* \* \* \* \*